United States Patent [19]

Lindemann et al.

[11] Patent Number: 5,786,375
[45] Date of Patent: Jul. 28, 1998

[54] HYDROXYETHYL-AZOLYL DERIVATIVES

[75] Inventors: Michael Lindemann, Hamm; Stefan Dutzmann, Hilden; Heinz-Wilhelm Dehne, Bonn; Gerd Hänssler, Leverkusen, all of Germany

[73] Assignee: Bayer Aktiengesellschaft, Leverkusen, Germany

[21] Appl. No.: 617,852

[22] PCT Filed: Sep. 6, 1994

[86] PCT No.: PCT/EP94/02964

§ 371 Date: Mar. 14, 1996

§ 102(e) Date: Mar. 14, 1996

[87] PCT Pub. No.: WO95/07896

PCT Pub. Date: Mar. 23, 1995

[30] Foreign Application Priority Data

Sep. 16, 1993 [DE] Germany .................. 43 31 476.7
Jun. 7, 1994 [DE] Germany .................. 44 19 812.4

[51] Int. Cl.$^6$ .................. A01N 43/653; C07D 249/08
[52] U.S. Cl. .................. 514/383; 514/184; 548/110; 548/267.8; 548/268.6
[58] Field of Search .................. 578/110, 267.8, 578/268.6; 514/184, 383

[56] References Cited

U.S. PATENT DOCUMENTS

| | | | |
|---|---|---|---|
| 4,911,746 | 3/1990 | Holmwood et al. | 71/92 |
| 4,913,727 | 4/1990 | Stroech et al. | 71/92 |
| 4,927,839 | 5/1990 | Parry et al. | 514/383 |
| 4,980,367 | 12/1990 | Cuomo et al. | 514/383 |
| 4,983,208 | 1/1991 | Stroech et al | 71/92 |

OTHER PUBLICATIONS

Cram and Hammond, "Organic Chemistry", McGraw-Hill Book Co NY (1964) 2nd Ed. pp. 546–567.

*Primary Examiner*—Patricia L. Morris
*Attorney, Agent, or Firm*—Sprung Kramer Schaefer & Briscoe

[57] ABSTRACT

Hydroxyethyl-azolyl derivative of the formula (I):

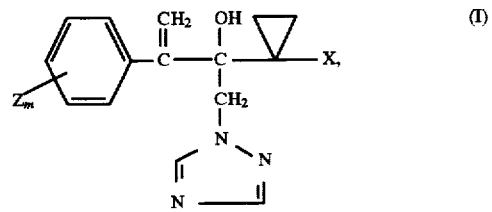

in which x represents hydrogen, halogen, alkyl having 1 to 4 carbon atoms or alkoxy having 1 to 4 carbon atoms, z represents halogen, alkyl having 1 to 4 carbon atoms, halogenoalkyl having 1 to 4 carbon atoms and 1 to 5 halogen atoms, alkoxy having 1 to 4 carbon atoms, halogenoalkoxy having 1 to 4 carbon atoms and 1 to 5 halogen atoms, nitro, or phenyl which is optionally monosubstituted to trisubstituted by identical or different halogen atoms, and m represents the numbers 0, 1, 2 or 3, and their acid addition salts and metal salt complexes thereof, are useful to combat microbes in plant protection and in the preservation of materials. Also, disclosed are processes for the preparation of the compounds of formula (I), and intermediates useful in such processes.

3 Claims, No Drawings

HYDROXYETHYL-AZOLYL DERIVATIVES

The present invention relates to new hydroxyethyl-azolyl derivatives, a process for their preparation, and to their use as microbicides in plant protection and in the protection of materials.

It has already been disclosed that a large number of hydroxyethyl-azolyl derivatives have fungicidal properties (cf. EP-OS (European Published Specification) 0 251 086, WO 89-05581 and WO 91-12000). 2-(2-Chlorophenyl)-3-(2,4-dichlorophenyl)-3-hydroxy-4-(1,2,4-triazol-1-yl)-but-1-ene and 2-(2-fluorophenyl)-3-(4-chlorophenyl)-3-hydroxy-4-(1,2,4-triazol-1-yl)-but-1-ene, for example, can be used for combating fungi. In some cases, however, the activity of these substances leaves something to be desired when low application rates are used.

New hydroxyethyl-azolyl derivatives of the formula

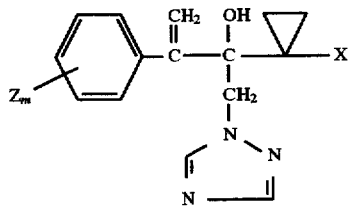

in which x represents hydrogen, halogen, alkyl having 1 to 4 carbon atoms or alkoxy having 1 to 4 carbon atoms, z represents halogen, alkyl having 1 to 4 carbon atoms, halogenoalkyl having 1 to 4 carbon atoms and 1 to 5 halogen atoms, alkoxy having 1 to 4 carbon atoms, halogenoalkoxy having 1 to 4 carbon atoms and 1 to 5 halogen atoms, nitro, or phenyl which is optionally monosubstituted to trisubstituted by identical or different halogen atoms, and m represents the numbers 0, 1, 2 or 3, and their acid addition salts and metal salt complexes have now been found.

The substances according to the invention contain an asymmetrically substituted carbon atom. They can therefore be obtained in the forms of optical isomers. The present invention relates to the individual isomers and also to their mixtures.

Furthermore, it has been found that hydroxyethyl-azolyl derivatives of the formula (I) and their acid addition salts and metal salt complexes are obtained when a) butenol derivatives of the formula

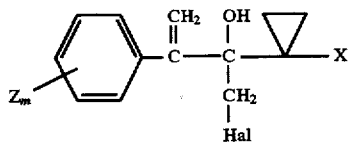

in which

X, Z and m have the abovementioned meanings and Hal represents chlorine or bromine, or b) oxiranes of the formula

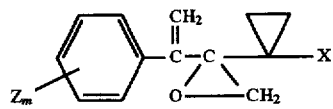

in which

X, Z and m have the abovementioned meanings, are reacted with 1,2,4-triazole of the formula

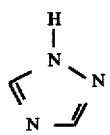

in the presence of an acid-binding agent and in the presence of a diluent and, if appropriate, the resulting compounds of the formula (I) are subsequently subjected to an addition reaction with an acid or a metal salt.

Finally, it has been found that the new hydroxyethyl-azolyl derivatives of the formula (I) and their acid addition salts and metal salt complexes have very good microbicidal properties and can be employed both in plant protection and in the protection of materials.

Surprisingly, the substances according to the invention have better microbicidal activity both in plant protection and in the protection of materials than the previously known compounds of the same direction of action and the most similar constitution. Thus, the substances according to the invention have superior fungicidal properties compared with, for example, 2-(2-chlorophenyl)-3-(2,4-dichlorophenyl)-3-hydroxy-4-(1,2, 4-triazol-1-yl)-but-1-ene and 2-(2-fluorophenyl)-3-(4-chlorophenyl) -3-hydroxy-4-(1, 2,4-triazol-1-yl) -but-1-ene.

Formula (I) provides a general definition of the hydroxyethyl-azolyl derivatives according to the invention.

x preferably represents hydrogen, fluorine, chlorine, methyl, ethyl, n-propyl, isopropyl, methoxy and ethoxy.

z preferably represents fluorine, chlorine, bromine, methyl, ethyl, n-propyl, isopropyl, n-butyl, sec-butyl, iso-butyl, tert-butyl, trichloromethyl, trifluoromethyl, difluoromethyl, methoxy, ethoxy, trifluoromethoxy, difluoromethoxy, nitro, or represents phenyl which is optionally monosubstituted or disubstituted by identical or different substituents from the series comprising fluorine and/or chlorine.

m preferably represents the numbers 0, 1, 2 or 3. If m represents 2 or 3, Z can represent identical or different radicals.

Other preferred substances according to the invention are addition products of acids and those hyroxyethyl-azolyl derivatives of the formula (I) in which X, Z and m have the meanings given as being preferred.

The acids which can be subjected to the addition reaction preferably include hydrohalic acids, such as, for example, hydrochloric acid and hydrobromic acid, in particular hydrochloric acid, furthermore phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and also sulphonic acids, such as, for example, p-toluenesulphonic acid, 1,5-naphthalenedisulphonic acid or camphorsulphonic acid, saccharin and thiosaccharin.

Other preferred compounds according to the invention are addition products of salts of metals from main group II to IV and sub-groups I and II and IV to VIII of the Periodic System of the Elements and those hydroxyethyl-azolyl derivatives of formula (I) in which X, Z and m have the meanings given as being preferred.

Particularly preferred in this context are salts of copper, zinc, manganese, magnesium, tin, iron and nickel. Suitable anions of these salts are those which are derived from those acids which lead to physiologically acceptable addition products. Particularly preferred acids of this type are, in this context, the hydrohalic acids, such as, for example, hydrochloric acid and hydrobromic acid, furthermore phosphoric acid, nitric acid and sulphuric acid.

Substances which may be mentioned as examples of hydroxyethyl-azolyl derivatives of the formula (I) are those listed in the table below.

TABLE 1

| $Z_m$ | X | $Z_m$ | X |
|---|---|---|---|
| 2-Cl | H | 2-OCH$_3$ | Cl |
| 4-Cl | CH$_3$ | 4-OCH$_3$ | Cl |
| 2,3-Cl$_2$ | Cl | 2-CF$_3$ | Cl |
| 2,4-Cl$_2$ | Cl | 4-CF$_3$ | Cl |
| 2,4-Cl$_2$ | F | 2-OCF$_3$ | Cl |
| 2,6-Cl$_2$ | F | 4-OCF$_3$ | Cl |
| 2,6-Cl$_2$ | Cl | 2-OCHF$_2$ | Cl |
| 2-F | H | 4-OCHF$_2$ | Cl |
| 2-F | CH$_3$ | 2-NO$_2$ | Cl |
| 2,4-F$_2$ | Cl | 4-NO$_2$ | Cl |
| 2,4-F$_2$ | F | 4-⌬ | Cl |
| 2-Cl | OCH$_3$ | 4-⌬-Cl | Cl |
| 2-F | OCH$_3$ | 2-OCH$_3$ | F |
| 2-Br | Cl | 4-OCH$_3$ | F |
| 2-Br | F | 2-CF$_3$ | F |
| 3-F | Cl | 4-CF$_3$ | F |
| 3-Br | Cl | 2-OCF$_3$ | F |
| 4-Br | Cl | 4-OCF$_3$ | F |
| 2-CH$_3$ | Cl | | |

If 1-chloro-2-(1-chlorocyclopropyl)-3-(2-fluorophenyl)-but-3-en-2-ol and 1,2,4-triazole are used as starting substances, the course of variant (a) of the process according to the invention can be illustrated by the following equation:

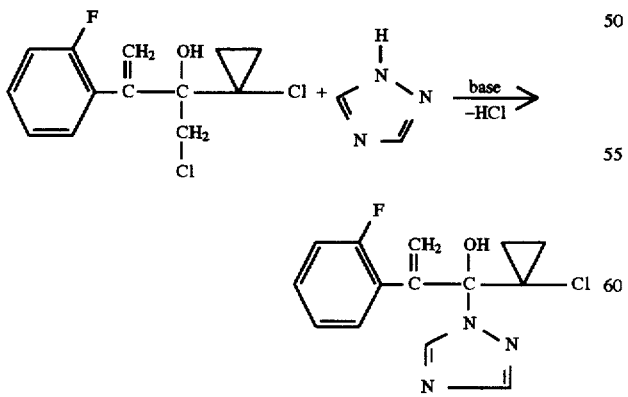

If 2-(α-styryl)-2-(1-chloro-cyclopropyl)-oxirane and 1,2,4-triazole are used as starting substances, the course of variant (b) of the process according to the invention can be illustrated by the following equation:

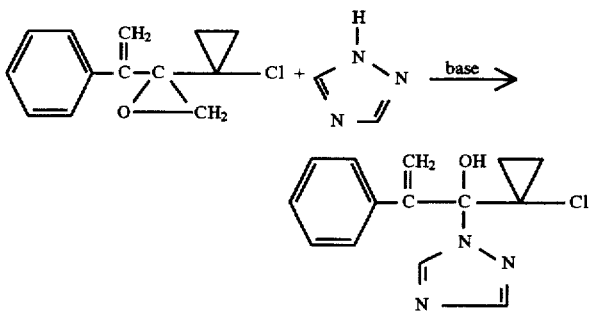

Formula (II) provides a general definition of the butenol derivatives required as starting substances in variant (a) of the process according to the invention. In this formula, X, Z and m preferably have those meanings which have already been mentioned in connection with the description of the substances of the formula (I) according to the invention as being preferred for these radicals or this index. Hal represents chlorine or bromine.

The butenol derivatives of the formula (II) are as yet unknown. They can be prepared by reacting cyclopropyl ketones of the formula

in which

X and Hal have the abovementioned meanings, with organometal compounds of the formula

in which

Z and m have the abovementioned meanings, in the presence of a diluent.

The cyclopropyl ketones of the formula (V) required as starting substances for the preparation of the butenol derivatives of the formula (II) by the above process are known (cf. EP-OS (European Published Specification) 0 297 345).

The organometal compounds of the formula (VI) required as reactants in the above process for the preparation of butenol derivatives of the formula (II) are known or can be prepared by methods known in principle (cf. J. Org. Chem. 41 (1976), 3725). For example, these substances are obtained by reacting styrene derivatives of the formula

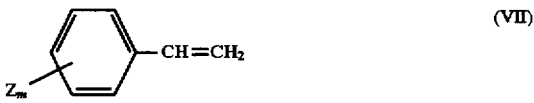

in which z and m have the abovementioned meanings, with bromine in the presence of a diluent, such as carbon tetrachloride, chloroform or dichloromethane, at temperatures between 0° C. and 30° C., reacting the resulting bromides of the formula

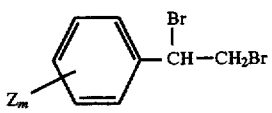

in which

Z and m have the abovementioned meanings, in the presence of a diluent, such as, for example, toluene, tetrahydrofuran or dioxane, and in the presence of a base, such as, for example, diazabicyclononene (DBN), diazabicycloundecene (DBU) or potassium hydroxide, in the presence of a phase transfer catalyst, at temperatures between 0° C. and 130° C., and reacting the resulting bromostyrene derivatives of the formula

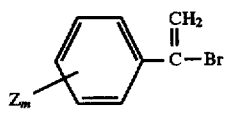

in which

Z and m have the abovementioned meanings, with magnesium turnings in the presence of a diluent, such as diethyl ether or tetrahydrofuran, at temperatures between 0° C. and 70° C.

Suitable diluents in the above process for the preparation of butenol derivatives of the formula (II) are all inert organic solvents which are customary for reactions of this type. Ethers, such as diethyl ether, tetrahydrofuran and dioxane, can preferably be used.

When carrying out the above process for the preparation of butenol derivatives of the formula (II), the reaction temperatures can be varied within a certain range. In general, the process is carried out at temperatures between –80° C. and +60° C.

The above process for the preparation of butenol derivatives of the formula (II) is generally carried out under atmospheric pressure. However, it is also possible to carry out the process under elevated or reduced pressure.

When carrying out the above process for the preparation of butenol derivatives of the formula (II), 1 to 1.2 mol of organometal compound of the formula (VI) are generally employed per 1 mol of cyclopropyl ketone of the formula (V), and this organometal compound is expediently prepared immediately prior to use and processed in situ. Working-up is carried out by customary methods. In general, a procedure is followed in which the mixture is first acidified and treated with water, and the organic phase is then separated off, washed, dried and then concentrated.

Formula (III) provides a general definition of the oxiranes required as starting substances in variant (b) of the process according to the invention. In this formula, X, Z and m preferably have those meanings which have already been mentioned in connection with the description of the substances of the formula (I) according to the invention as being preferred for these radicals or this index.

The oxiranes of the formula (III) are as yet unknown. They can be prepared by c) reacting butenol derivatives of the formula

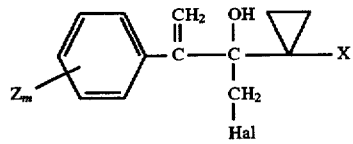

in which

X, Z, m and Hal have the abovementioned meanings, with bases in the presence of a diluent, or d) reacting ketones of the formula

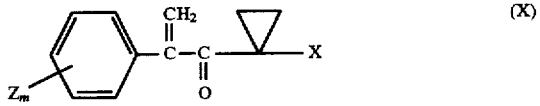

in which

X, Z and m have the abovementioned meanings, with dimethylsulphonium methylide of the formula $$(CH_3)_2{}^{\oplus}S{}^{\ominus}CH_2 \qquad (XI)$$

in the presence of a diluent.

Bases which are suitable for the preparation of oxiranes of the formula (III) by the above process (c) are all inorganic and organic bases which are conventionally suitable for reactions of this type. The following can preferably be used: alkali metal carbonates, such as sodium carbonate and potassium carbonate, furthermore alkali metal hydroxides, such as sodium hydroxide and potassium hydroxide, moreover alkali metal alcoholates, such as sodium methylate, sodium ethylate, potassium methylate, potassium ethylate and potassium tert-butylate, and furthermore lower tertiary alkylamines, cycloalkylamines and aralkylamines, such as, in particular, triethylamine.

Diluents which are suitable for the preparation of oxiranes of the formula (III) by the above process (c) are all customary inert organic solvents. The following can preferably be used: nitriles, such as acetonitrile, furthermore aromatic hydrocarbons, such as benzene, toluene and dichlorobenzene, moreover formamides, such as dimethylformamide, and also strongly polar solvents, such as dimethyl sulphoxide and hexamethylphosphoric triamide.

When preparing oxiranes of the formula (III) by the above process (c), the reaction temperatures can be varied within a certain range. In general, the process is carried out at temperatures between 0° C. and 100° C., preferably between 20° C. and 60° C.

The above process (c) for the preparation of oxiranes of the formula (III) is generally carried out under atmospheric pressure. However, the process can also be carried out under elevated or reduced pressure.

When carrying out the above process (c) for the preparation of oxiranes of the formula (III), 1 to 3 mol of base are generally employed per 1 mol of butenol derivative of the formula (II). Working-up is carried out by customary methods.

Formula (X) provides a general definition of the ketones required as starting substances when carrying out the above process (d) for the preparation of oxiranes of the formula (III). In this formula, X, Z and m preferably have those meanings which have already been mentioned in connection with the description of the substances of the formula (I) according to the invention as being preferred for these radicals or this index.

The ketones of the formula (X) were hitherto unknown. They can be prepared by reacting benzyl ketones of the formula

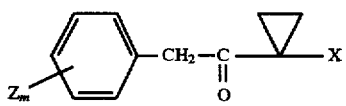

in which

X, Z and m have the abovementioned meanings, either

α) with bis-(dimethylamino)-methane of the formula

in the presence of acetic anhydride or glacial acetic acid, or

β) with paraformaldehyde or formalin in the presence of a catalyst and in the presence of a diluent.

Formula (XII) provides a general definition of the benzyl ketones required as starting substances in the preparation of the ketones of the formula (X) by the above process. In this formula, X, Z and m preferably have those meanings which have already been mentioned in connection with the description of the substances of the formula (I) according to the invention as being preferred for these radicals or this index.

The benzyl ketones of the formula (XII) have been disclosed or can be prepared by methods known in principle (cf. EP-OS [European Published Specification] 0 461 483 and EP-OS [European Published Specification] 0 461 502).

The substances required as reactants when carrying out the above process (d), that is to say bis-(dimethylamino)-methane, of the formula (XIII), and paraformaldehyde or formalin (aqueous formaldehyde solution having a formaldehyde content of 37%) are known.

When carrying out variant (α) of the above process for the preparation of ketones of the formula (X), the reaction temperatures can be varied within a substantial range. In general, the process is carried out at temperatures between 20° C. and 120° C., preferably between 30° C. and 110° C.

When carrying out variant (α) and also variant (β) of the above process for the preparation of ketones of the formula (X), this is generally done under atmospheric pressure. However, the process can also be carried out under elevated or reduced pressure.

When carrying out variant (α) of the above process for the preparation of ketones of the formula (X), 3 to 4 moles of bis-(dimethylamino)-methane, of the formula (XIII), are generally employed per 1 mol of benzyl ketone of the formula (XII). Working-up is carried out by customary methods.

Suitable catalysts for carrying out variant (β) of the above process for the preparation of ketones of the formula (X) are all reaction accelerators which are customary for such reactions. Alkali metal hydroxides, such as sodium hydroxide or potassium hydroxide, can preferably be used.

Diluents which are suitable for carrying out variant (β) of the above process for the preparation of ketones of the formula (X) are all inert, organic solvents which are customary for such reactions. Alcohols, such as methanol or ethanol, can preferably be used.

When carrying out variant (β) of the above process for the preparation of ketones of the formula (X), the reaction temperatures can be varied within a certain range. In general, the process is carried out at temperatures between 10° C. and 40° C., preferably at room temperature.

When carrying out variant (β) of the above process for the preparation of ketones of the formula (X), 1.5 to 2.5 equivalents of paraformaldehyde or formalin and an equivalent amount of catalyst are generally employed per 1 mol of benzyl ketone of the formula (XII). —Working-up is carried out by customary methods.

Dimethylsulphonium methylide, of the formula (XI), which is required as reactant for carrying out the above process (d) for the preparation of oxiranes of the formula (III), is known (cf. Heterocycles 8 397 (1977)). In the above reaction, it is employed in the freshly prepared state by preparing it in situ, for example from trimethylsulphonium halide or trimethylsulphonium methylsulphate, in the presence of a strong base, such as, for example, sodium hydride, sodium amide, sodium methylate, potassium tert-butylate or potassium hydroxide, in the presence of a diluent, such as tert-butanol or dimethyl sulphoxide.

Suitable diluents for carrying out the above process (d) for the preparation of oxiranes of the formula (III) are inert organic solvents. The following can preferably be used: alcohols, such as tert-butanol, ethers, such as tetrahydrofuran or dioxane, furthermore aliphatic and aromatic hydrocarbons, such as benzene, toluene or xylene, and also strongly polar solvents, such as dimethyl sulphoxide.

When carrying out the above process (d) for the preparation of oxiranes of the formula (III), the reaction temperatures can be varied within a substantial range. In general, the process is carried out at temperatures between 0° C. and 100° C., preferably between 10° C. and 60° C.

When carrying out the above process (d) for the preparation of oxiranes of the formula (III), 1 to 3 moles of dimethylsulphonium methylide, of the formula (XI), are generally employed per 1 mol of ketone of the formula (X). —Working-up is carried out by customary methods.

Suitable acid-binding agents for carrying out the process according to the invention are all customary inorganic and organic bases. The following can preferably be used: alkali metal carbonates, such as sodium carbonate and potassium carbonate, furthermore alkali metal hydroxides, such as sodium hydroxide and potassium hydroxide, more-over alkali metal alcoholates, such as sodium methylate, sodium ethylate, potassium methylate, potassium ethylate and potassium tert-butylate, and furthermore lower tertiary alkylamines, cycloalkylamines and aralkylamines, such as, in particular, triethylamine.

Suitable diluents for carrying out the process according to the invention are all customary inert organic solvents. The following can preferably be used: nitriles, such as acetonitrile, furthermore aromatic hydrocarbons, such as benzene, toluene and dichlorobenzene, moreover formamides, such as dimethylformamide, and also strongly polar solvents, such as dimethyl sulphoxide and hexamethylphosphoric triamide.

When carrying out the process according to the invention, the reaction temperatures can be varied within a substantial range. In general, the process is carried out at temperatures between 0° C. and 130° C., preferably between 40° C. and 120° C.

Again, the process according to the invention is generally carried out under atmospheric pressure. However, it is also possible to carry out the process under elevated or reduced pressure.

When carrying out the process according to the invention, 1 to 4 mol of 1,2,4-triazole of the formula (IV) and 0.3 to 3 mol of acid-binding agent are generally employed per 1 mol of butenol derivative of the formula (II) or oxirane of the formula (III). Working-up is carried out by customary methods. In general, a procedure is followed in which the reaction mixture is concentrated, the residue which remains is taken up in an organic solvent which is sparingly miscible with water, and the mixture is washed with water, dried and then concentrated. If appropriate, the product which remains can be subjected to further purification methods.

The hydroxyethyl-azolyl derivatives of the formula (I) according to the invention can be converted into acid addition salts or metal salt complexes.

Acids which are suitable for the preparation of acid addition salts of the compounds of the formula (I) are preferably those which have already been mentioned in connection with the description of the acid addition salts according to the invention as being preferred acids.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and, if appropriate, purified by washing with an inert organic solvent.

Salts which are preferably suitable for the preparation of metal salt complexes of the compounds of the formula (I) are preferably those metal salts which have already been mentioned in connection with the description of the metal salt complexes according to the invention as being preferred metal salts.

The metal salt complexes of the compounds of the formula (I) can be obtained in a simple manner by customary processes, for example by dissolving the metal salt in alcohol, for example ethanol, and adding the solution to compounds of the formula (I). Metal salt complexes can be isolated in a known manner, for example by filtration, and, if appropriate, they can be purified by recrystallization.

The active compounds according to the invention have a powerful microbicidal activity and can be employed for combating undesirable microorganisms, such as fungi and bacteria, in plant protection and in the protection of materials.

Fungicides are employed in plant protection for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:
Xanthomonas species, such as Xanthomonas;
Pseudomonas species, such as *Pseudomonas lachrymans;*
Erwinia species, such as *Erwinia amylovora;*
Pythium species, such as *Pythium ultimum;*
Phytophthora species, such as *Phytophthora infestans;*
Pseudoperonospora species, such as *Pseudoperonospora humuli* or *Pseudoperonospora cubensis;*
Plasmopara species, such as *Plasmopara viticola;*
Peronospora species, such as *Peronospora pisi* or *P. brassicae;*
Erysiphe species, such as *Erysiphe graminis;*
Sphaerotheca species, such as *Sphaerotheca fuliginea;*
Podosphaera species, such as *Podosphaera leucotricha;*
Venturia species, such as *Venturia inaequalis;*
Pyrenophora species, such as *Pyrenophora teres* or *P. graminea* (conidia form: Drechslera, syn: Helminthosporium);
Cochliobolus species, such as *Cochliobolus sativus* (conidia form: Drechslera, syn: Helminthosporium);
Uromyces species, such as *Uromyces appendiculatus;*
Puccinia species, such as *Puccinia recondita;*
Tilletia species, such as *Tilletia caries;*
Ustilago species, such as *Ustilago nuda* or *Ustilago avenae;*
Pellicularia species, such as *Pellicularia sasakii;*
Pyricularia species, such as *Pyricularia oryzae;*
Fusarium species, such as *Fusarium culmorum;*
Botrytis species, such as *Botrytis cinerea;*
Septoria species, such as *Septoria nodorum;*
Leptosphaeria species, such as *Leptosphaeria nodorum;*
Cercospora species, such as *Cercospora canescens;*
Alternaria species, such as *Alternaria brassicae* and
Pseudocercosporella species for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

In particular, the active compounds according to the invention are suitable for combating *Pyricularia oryzae* and *Pellicularia sasakii* in rice and for combating cereal diseases, such as *Leptosphaeria nodorum, Cochliobolus sativus, Pyrenophora teres, Pseudocercosporella herpotrichoides,* Erysiphe and Fusarium species. Moreover, the substances according to the invention display a very good and broad in-vitro activity.

In the protection of materials, the substances according to the invention can be employed for protecting industrial materials against attack and destruction by undesirable microorganisms.

Industrial materials in the present context are to be understood as meaning non-live materials which have been prepared for use in technology. Examples of industrial materials which are to be protected against microbial change or destruction by active compounds according to the invention are glues, sizes, paper and board, textiles, leather, wood, paints and plastic articles, cooling lubricants and other materials which can be attacked or decomposed by microorganisms. Parts of production plants, for example cooling water circuits, which can be adversely affected by multiplication of microorganisms, may also be mentioned in the scope of the materials to be protected. Industrial materials which may preferably be mentioned within the scope of the present invention are glues, sizes, paper and board, leather, wood, paints, cooling lubricants and heat transfer fluids, very particularly wood.

Examples of microorganisms which can cause degradation or change of the industrial materials are bacteria, fungi, yeasts, algae and slime organisms. The active compounds according to the invention are preferably active against fungi, in particular moulds, wood-discolouring and wood-destroying fungi (Basidiomycetes) and against slime organisms and algae.

Examples which may be mentioned are microorganisms from the following genera:
Alternaria, such as *Alternaria tenius,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,*
Staphylococcus, such as *Staphylococcus aureus.*

The substances according to the invention can be converted into the customary formulations, such as solutions, emulsions, suspensions, powders, foams, pastes, granules, aerosols, very fine capsules in polymeric substances and in coating compositions for seeds, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butenol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water, by liquefied gaseous extenders or carriers are meant liquids which are gaseous at ambient temperature and under atmospheric pressure, for example aerosol propellants, such as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for is example alkylaryl polyglycol ethers, alkylsulphonates, alkyl sulphates, arylsulphonates as well as albumen hydrolysis products, as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colourants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

When used in plant protection, the active compounds according to the invention, as such or in their formulations, can also be used in the form of mixture with known fungicides, bactericides, acaricides, nematicides or insecticides, for example to broaden the spectrum of action or to prevent the build-up of resistance. In some cases, synergistic effects are observed, which means that the activity of the mixture is greater than the total of the activities of the individual components.

Examples of components in the mixtures are the following substances:
Fungicides:
2-aminobutane; 2-anilino-4-methyl-6-cyclopropyl-pyrimidine; 2',6'-dibromo-2-methyl-4'-trifluoromethoxy-4'-trifluoro-methyl-1,3-thiazol-5-carboxanilide; 2,6-dichloro-N-(4-trifluoromethylbenzyl)-benzamide; (E)-2-methoxyimino-N-methyl-2-(2-phenoxyphenyl) acetamide; 8-hydroxyquinoline sulphate; methyl (E)-2-{2-[6-(2-cyanophenoxy)-pyrimidin-4-yloxy]phenyl}-3-methoxyacrylate; methyl (E)-methoximino[alpha-(o-tolyloxy)-o-tolyl]-acetate; 2-phenylphenol (OPP), aldimorph, ampropylfos, anilazine, azaconazole,
benalaxyl, benodanil, benomyl, binapacryl, biphenyl, bitertanol, blasticidin-S, bromuconazole, bupirimate, buthiobate,
calcium polysulphide, captafol, captan, carbendazim, carboxin, quinomethionate, chloroneb, chloropicrin, chlorothalonil, chlozolinate, cufraneb, cymoxanil, cyproconazole, cyprofuram,
dichlorophen, diclobutrazole, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon,
edifenphos, epoxyconazole, ethirimol, etridiazole,
fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetylaluminium, fthalide, fuberidazole, furalaxyl, furmecyclox,
guazatine,
hexachlorobenzene, hexaconazole, hymexazole,
imazalil, imibenconazole, iminoctadine, iprobenfos (IBP), iprodione, isoprothiolane,
kasugamycin, copper preparations, such as: copper hydroxide, copper naphthenate, copper oxychloride, copper sulphate, copper oxide, oxine copper and Bordeaux mixture,
mancopper, mancozeb, maneb, mepanipyrim, mepronil, metalaxyl, metconazole, methasulfocarb, methfuroxam, metiram, metsulfovax, myclobutanil,
nickel dimethyldithiocarbamate, nitrothal-isopropyl, nuarimol,
ofurace, oxadixyl, oxamocarb, oxycarboxin,
perfurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon,
quintozene (PCNB),
sulphur and sulphur preparations,
tebuconazole, tecloftalam, tecnazen, tetraconazole, thibendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole,
validamycin A, vinclozolin,
zineb, ziram.
Bactericides:
bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations.
Insecticides/Acaricides/Nematicides:
abamectin, abamectin, AC 303 630, acephate, acrinathrin, alanycarb, aldicarb, alphamethrin, amitraz, avermectin, AZ 60541, azadirachtin, azinphos A, azinphos M, azocyclotin,
Bacillus thuringiensis, bendiocarb, benfuracarb, bensultap, betacyluthrin, bifenthrin, BPMC, brofenprox, bromophos A, bufencarb, buprofezin, butocarboxin, butylpyridaben,
cadusafox, carbaryl, carbofuran, carbophenothion, carbosulphan, cartap, CGA 157 419, CGA 184699, chloethocarb, chlorethoxyfos, chlorfenvinphos, chlorfluazuron, chlormephos, chlorpyrifos, chlorpyrifos M, cisresmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethione, diflubenzuron, dimethoate, dimethylvinphos, dioxathion, disulphoton, edifenphos, emamectin, esfenvalerate, ethiofencarb, ethione, ethofenprox, ethoprophos, etofenprox, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathione, ivemectin, lambda-cyhalothrin, lufenuron, malathion, mecarbam, meavinphos, mesulphenphos, metaldehyde, methacrifos, methamidophos, methidathion, methiocarb, methomyl, metolcarb, milbemectin, monocrotophos, moxidectin, naled, NC 184, NI 25, nitenpyram omethoate, oxamyl, oxydemethon M, oxydeprofos, parathion A, parathion M, permethrin, phenthoate, phorate, phosalone, phosmet, phospham;don, phoxim, pirimicarb, pirimiphos M, pirimiphos A, profenofos, promecarb, propaphos, propoxur, prothiofos, prothoate, pymetrozin, pyrachlophos, pyradaphenthion, pyresmethrin, pyrethrum, pyridaben, pyrimidifen, pyriproxifen, quinalphos,

RH 5992, salithion, sebufos, silafluofen, sulphotep, sulprofos, tebufenozid, tebufenpyrad, tebupirimphos, teflubenzuron, tefluthrin, temephos, terbam, terbufos, tetrachlorvinphos, thiafenox, thiodicarb, thiofanox, thiometon, thionazin, thuringiensin, tralomethrin, triarathen, triazophos, triazuron, trichlorfon, triflumuron, trimethacarb, vamidothio, XMC, xylylcarb, zetamethrin.

A mixture with other known active compounds, such as herbicides or fertilizers and growth regulators, is also possible.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound preparation or the active compound itself into the soil. The seeds of the plants can also be treated.

In the treatment of parts of plants, the active compound concentrations in the use forms may be varied within a substantial range: they are, in general, between 1 and 0.0001% by weight, preferably between 0.5 and 0.001% by weight.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The compositions used for the protection of industrial materials generally contain 1 to 95%, preferably 10 to 75%, of active compounds.

The use concentrations of the active compounds according to the invention depend on the nature and the occurrence of the microorganisms to be combated and on the composition of the material to be protected. The optimum application rate can be determined by test series. In general, the use concentrations are in the range of 0.001 to 5% by weight, preferably 0.05 to 1.0% by weight, relative to the material to be protected.

The activity and the spectrum of action of the active compounds to be used according to the invention in the protection of materials, or of the compositions, concentrates or, quite generally, formulations which can be prepared with these active compounds, can be increased by adding, if appropriate, other antimicrobially active compounds, fungicides, bactericides, herbicides, insecticides or other active compounds to widen the spectrum of action or to achieve specific effects, such as, for example, an additional protection against insects. These mixtures can have a broader spectrum of action than the compounds according to the invention.

In many cases, this results in synergistic effects, that is to say that the activity of the mixture exceeds the activity of the individual components. Examples of particularly advantageous components in the mixtures are the following compounds:

Sulphenamides, such as dichlorfluanid (Euparen), tolyfluanid (Methyleuparen), folpet, fluorfolpet;

benzimidazoles, such as carbendazim (MBC), benomyl, fuberidazole, thiabendazole or their salts;

thiocyanates, such as thiocyanatomethylthiobenzothiazole (TCMTB), methylene bisthiocyanate (MBT);

quaternary ammonium compounds, such as benzyldimethyltetradecylammonium chloride, benzyl-dimethyl-dodecylammonium chloride, dodecyl-dimethylammonium chloride;

morpholine derivatives, such as $C-C_{14-4}$-alkyl-2,6-dimethyl-morpholine homologues (tridemorph) (±)-cis-4-[tert-butylphenyl)-2-methylpropyl]-2,6-dimethylmorpholine (fenpropimorph), falimorph;

phenols, such as o-phenylphenol, tribromophenol, tetrachlorophenol, pentachlorophenol,3-methyl-4-chlorophenol, dichlorophen, chlorophen or their salts;

azoles, such as triadimefon, triadimenol, bitertanol, tebuconazole, propiconazole, azaconazole, hexaconazole, prochloraz, cyproconazole, 1-(2-chlorophenyl)-2-(1-chlorocyclopropyl) -3-(1, 2,4-triazol-1-yl)-propan-2-ol or 1-(2-chlorophenyl)-2-(1,2,4-triazol-1-yl-methyl)-3, 3-dimethyl-butan-2-ol.

Iodopropargyl derivatives, such as iodopropargyl butylcarbamate (IPBC), iodopropargyl chlorophenylformal, iodopropargyl phenylcarbamate, iodopropargyl hexylcarbamate, iodopropargyl cyclohexylcarbamate and iodopropargyloxyethyl phenylcarbamate;

iodine derivatives, such as diiodomethyl-p-aryl sulphones; for example diiodomethyl-p-tolylsulphone;

bromine derivatives, such as bromopol;

isothiazolines, such as N-methylisothiazolin-3-one, 5-chloro-N-methylisothiazolin-3-one, 4,5-dichloro-N-octylisothiazolin-3-one, N-octylisothiazolin-3-one (octilinone); benzoisothiazolinone, cyclopenteneisothiazoline;

pyridines, such as 1-hydroxy-2-pyridinethione (and their sodium, iron, manganese and zinc salts), tetrachloro-4-methylsulphonylpyridine;

metal soaps, such as tin naphthenate, tin octoate, tin 2-ethylhexanoate, tin oleate, tin phosphate, tin benzoate, copper naphthenate, copper octoate, copper 2-ethylhexanoate, copper oleate, copper phosphate, copper benzoate, zinc naphthenate, zinc octoate, zinc 2-ethylhexanoate, zinc oleate, zinc phosphate and zinc benzoate, and oxides, such as TBTO, Cu$_2$O, CuO, ZnO;

organotin compounds, such as tributyltin naphtenate and tributyltin oxide;

dialkyldithiocarbamate, such as sodium and zinc salts of dialkyldithiocarbamates, tetramethyltiuram disulphide (TMTD);

nitriles, such as 2,4,5,6-tetrachloroisophthalonitrile (chlorothalonil) and other microbicides having an activated halogen group, such as Cl—Ac, MCA, tectamer, bromopol, bromidox;

benzothiazoles, such as 2-mercaptobenzothiazole; see above dazomet;

quinolines, such as 8-hydroxyquinoline;

formaldehyde-releasing compounds, such as benzyl alcohol mono(poly)hemiformal, oxazolidines, hexahydro-s-triazines, N-methylolchloroacetamide;

tris-N-(cyclohexyldiazeniumdioxy)-aluminium, N-(cyclohexyldiazeniumdioxy)-tributyltin or the potassium salts, bis-(N-cyclohexyl) diazinium-(dioxy-copper or aluminium)

Insecticides which are preferably added are:

Phosphoric esters, such as azinphos-ethyl, azinphosmethyl, 1-(4-chlorophenyl)-4-(O-ethyl, S-propyl)-phosphoryloxypyrazole (TIA-230), chlorpyrifos, coumaphos, demeton, demeton-S-methyl, diazinon, dichlorfos, dimethoate, ethoprophos, etrimfos, fenitrothion, fention, heptenophos, parathion, parathion-methyl, phosalone, phoxim, pirimiphos-ethyl, pirimiphos-methyl, profenofos, prothiofos, sulprofos, triazophos and trichlorphon.

Carbamates, such as aldicarb, bendiocarb, BMPC (2-(1-(methylpropyl) phenyl methylcarbamate), butocarboxim, butoxycarboxim, carbaryl, carbofuran, carbosulphan, cloethocarb, isoprocarb, methomyl, oxamyl, pirimicarb, promecarb, propoxur and thiodicarb.

Pyrethroids, such as allethrin, alphamethrin, bioresmethrin, byfenthrin (FMC 54800), cycloprothrin, cyfluthrin, decamethrione, cyhalothrin, cypermethrin, deltamethrin, alpha-cyano-3-phenyl-2-methylbenzyl-2, 2-dimethyl-3-(2-chloro-2-trifluoromethylvinyl) cyclopropanecarboxylate, fenpropathrin, fenfluthrin, fenvalerate, flucythrinate, flumethrin, fluvalinate, permethrin, and resmethrin; nitroimino compounds and nitromethylene compounds, such as 1-[(6-chloro-3-pyridinyl) -methyl]-4, 5-dihydro-N-nitro-1H-imidazole-2-amine (imidacloprid).

Organosilicon compounds, preferably dimethyl(phenyl)-silylmethyl 3-phenoxybenzyl ethers, such as, for example, dimethyl-(4-ethoxyphenyl)-silylmethyl 3-phenoxybenzyl ether or dimethyl(phenyl)-silylmethyl 2-phenoxy-6-pyridylmethyl ethers, such as, for example, dimethyl (9-ethoxyphenyl) -silylmethyl 2-phenoxy-6-pyridylmethyl ether or (phenyl [3-(3-phenoxyphenyl)propyl] (dimethyl)-silanes, such as, for example, (4-ethoxyphenyl)-[3-(4-fluoro-3-phenoxyphenyl)-propyl]dimethylsilane.

Other active compounds which are suitable are algicides, molluscicides, and active compounds against sea animals which colonize for example ships' bottom paints.

The preparation and the use of substances according to the invention are illustrated by the examples which follow.

PREPERATION EXAMPLES

Example 1

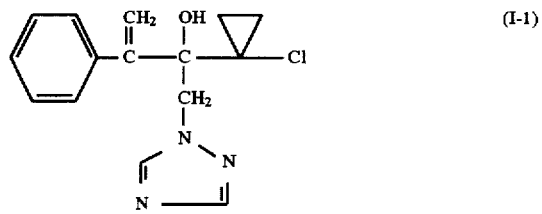

A solution of 5.2 g (20 mmol) of 1-chloro-2-(1-chlorocyclopropyl)-3-phenyl-but-3-en-2-ol, 5.2 g (75 mmol) of 1,2,4-triazole and 3.4 g (30 mmol) of potassium tert-butylate in 50 ml of dimethylformamide is stirred for 8 hours at 80° C. The reaction mixture is then concentrated by stripping off the solvent under reduced pressure. The residue which remains is taken up in ethyl acetate and washed with water, and the organic phase is dried over sodium sulphate and concentrated by stripping off the solvent under reduced pressure. The residue which remains is chromatographed on silica gel using ethyl acetate:cyclohexane=2:1 as the eluent. Concentration of the eluate gives 1.7 g (30% of theory) of 2-phenyl-3-(1-chlorocyclopropyl)-3-hydroxy-4-(1,2,4-triazol-1-yl)-but-1-ene.

$^1$H-NMR spectrum (200 MHz, CDCl$_3$, TMS) δ=0.2–0.5 (m, 2H); 0.75–0.95 (m, 2H), 4.43 (d, J=14 Hz, 1H); 4.9 (d, J=14 Hz, 1H); 5.36 (d, J=2 Hz, 1H); 5.65 (d, J=2 Hz, 1H), 7.3–7.5 (m, 5H), 8.0 (s, 1H), 8.22 (s, 1H) ppm Preparation of the starting substance:

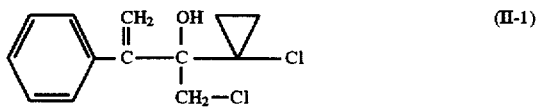

A solution of 5 g (25 mmol) of α-bromostyrene in 10 ml of absolute diethyl ether is added dropwise to a mixture of 0.7 g (30 mmol) of magnesium filings and 10 ml of diethyl ether under an argon atmosphere and with stirring at room temperature. After the addition has ended, the reaction mixture is refluxed for 1 hour. The resulting Grignard solution is added dropwise at room temperature with stirring to a solution of 3 g (20 mmol) of 1-chlorocyclopropyl chloromethyl ketone in 10 ml of diethyl ether. After the addition has ended, the mixture is refluxed for another 4 hours. The reaction mixture is subsequently treated with a saturated, aqueous ammonium chloride solution, the resulting mixture is poured into water, and this mixture is extracted repeatedly using diethyl ether. The combined organic phase are washed with saturated, aqueous sodium chloride solution, dried over sodium sulphate, and then concentrated by stripping off the solvent under reduced pressure. 5.0 g (97% of theory) of 1-chloro-2-(1-chlorocyclopropyl)-3-phenyl-but-3-en-2-ol are obtained.

Example 2

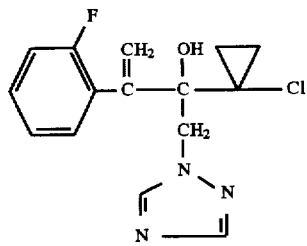
(I-2)

A solution of 59 g (0.25 mol) of 1-(1-chloro-cycloprop-1-yl)-1-[3-(2-fluoro-phenyl)-prop-1-en-2-yl]-oxirane in 100 ml of dimethylformamide is added dropwise at 80° C. with stirring to a solution of 52 g (0.75 mol) of 1,2, 4-triazole and 8.4 g (0.075 mol) of potassium tert-butylate in 500 ml of dimethylformamide. After the addition has ended, stirring is continued for 18 hours at 80° C. The reaction mixture is subsequently concentrated under reduced pressure and treated with water. The resulting mixture is extracted several times with ethyl acetate. The combined organic phases are dried over sodium sulphate and then concentrated under reduced pressure. The residue which remains is chromatographed on silica gel using ethyl acetate:cyclohexane=2:1 as eluent. Concentration of the eluate under reduced pressure gives 40 g (52% of theory) of 2-(2-fluorophenyl)-3-(1-chloro-cyclopropyl)-3-hydroxy-4-(1,2,4-triazol-1-yl)-but-1-ene.

$^1$H-NMR spectrum (200 MHZ, CDCl$_3$, TMS): δ=0.3–0.5 (m, 2H); 0.8–1.0 (m, 2H); 4.46 (d, J=14 Hz, 1H); 5.0 (d, J=14 Hz, 1H); 5.39 (d, J=1 Hz, 1H); 5.84 (d, J=1 Hz, 1H), 7.0–7.4 (m, 4H), 8.0 (s, 1H), 8.29 (s, 1H) ppm Preparation of Starting Substances:

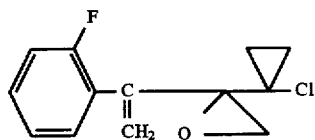

A solution of 66 g (0.33 mol) of trimethylsulphonium iodide in 400 ml of dimethyl sulphoxide is added dropwise at 0° C. to a mixture of 9.8 g (0.33 mol) of sodium hydride, 400 ml of dimethyl sulphoxide and 400 ml of tetrahydrofuran. After the addition has ended, stirring is continued for 5 minutes at 0° C., and 70 g (0.25 mol) of 2-(2-fluorophenyl)-3-(1-chloro-cycloprop-1-yl)-prop-1-en-3-one in 100 ml of dimethyl sulphoxide are then added. The reaction mixture is stirred first for 15 minutes at 0° C. and then for another 6 hours at room temperature. The reaction mixture is subsequently poured into ice-water and extracted repeatedly using ethyl acetate, and the combined organic phases are washed with water, dried over sodium sulphate and concentrated under reduced pressure. In this manner, 53 g (90%- of theory) of 1-(1-chloro-cycloprop-1-yl)-1-[3-(2-fluorophenyl)-prop-1-en-2-yl]-oxirane are obtained in the form of an oily product which is used for the subsequent synthesis without additional purification.

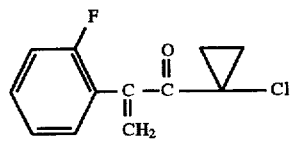
(X-1)

250 ml (2.65 mol) of acetic anhydride are added dropwise with stirring at room temperature to a mixture of 106 g (0.5 mol) of 1-chloro-cyclopropyl 2'-fluoro-benzyl ketone and 250 ml (1.8 mol) of bis-(dimethylamino)-methane. After the addition has ended, stirring of the reaction mixture is first continued for 1 hour at 90° C., and the mixture is then cooled to room temperature and poured into ice-water. The resulting mixture is extracted repeatedly using ethyl acetate. The combined organic phases are washed in succession with dilute, aqueous sodium hydrogen carbonate solution, then dried over sodium sulphate and concentrated under reduced pressure. In this manner, 107 g (95% of theory) of 2-(2-fluorophenyl) -3-(1-chloro-cycloprop-1-yl)prop-1-en-3-one are obtained in the form of an oily product which is used for the subsequent synthesis without additional purification.

The substances of the formula (I) listed in Table 2 below are also prepared by the methods indicated in Examples 1 and 2.

TABLE 2

(I)

| Example No. | $Z_m$ | X | Physical constant |
|---|---|---|---|
| 3 | 2-Cl | Cl | *) |
| 4 | 4-Cl | Cl | *) |
| 5 | 4-F | Cl | *) |
| 6 | 3-Cl | Cl | *) |
| 7 | — | F | *) |
| 8 | 2-Cl | F | *) |
| 9 | 4-Cl | F | *) |
| 10 | 2-OCHF$_2$ | F | *) |

*) The compounds were characterized by the $^1$H-NMR spectrum signals (200 MHz, CDCl$_3$, TMS) listed below.

Example 3

δ=0.3–0.6 (m, 2H); 0.8–1.1 (m, 2H), 4.40 (d, J=15 Hz, 1H); 5.02 (d, J=15 Hz, 1H); 5.37 (d, J=1 Hz, 1H); 5.90 (d, J=1 Hz, 1H); 7.0–7.5 (m, 4H), 7.97 (s, 1H), 8.29 (s, 1H) ppm

Example 4

δ=0.2–0.5 (m, 2H), 0.7–0.9 (m, 2H), 4.41 (d, J=15 Hz, 1H); 4.92 (d, J=15 Hz, 1H), 5.32 (d, J=1 Hz, 1H); 5.62 (d., J=1 Hz, 1H), 7.2–7.5 (m, 4H); 8.01 (s, 1H); 8.24 (s, 1H) ppm

Example 5

δ=0.3–1.3 (m, 4H) ; 3.6 (d, J=15 Hz, 1H) ; 4.1 (d, J=15 Hz, 1H); 5:25 (s, 1H); 5.39 (s, 1H); 7.0–7.5 (m, 4H); 7.85 (s, 1H); 8.27 (s, 1H) ppm

Example 6

δ=0.2–1.3 (m, 4H) ; 4.4 (d, J=14 Hz, 1H) ; 4.92 (d, J=14 Hz, 1H); 5.34 (d, J=1 Hz, 1H); 5.66 (d, J=1 Hz, 1H); 7.1–7.5 (m, 4H); 8.0 (s, 1H); 8.25 (s, 1H) ppm

Example 7

δ=0.3–0.6 (m, 2H); 0.75–1.1 (m, 2H); 4.43 (dd, J=13 and 2 Hz, 1H); 4.63 (dd, J=13 and 2 Hz 1H); 5.32 (d, J=1 Hz, 1H); 5.75 (d, J=1 Hz, 1H); 7.2–7.4 (m, 5H); 7.95 (s, 1H); 8.0 (s, 1H) ppm

Example 8

δ=0.2–0.6 (m, 2H) ; 0.75–1.05 (m, 2H); 4.49 (dd, J=13 and 2 Hz, 1H); 4.86 (dd, J=13 and 2 Hz, 1H); 5.35 (d, J=1

Hz, 1H); 5.92 (d, J=1 Hz, 1H); 7.2–7.5 (m, 4H); 7.89 (s, 1H); 8.13 (s, 1H) ppm

Example 9

δ=0.3–0.6 (m, 2H) ; 0.75–1.05 (m, 2H) ; 4.4 ( dd, J=13 and 2 Hz, 1H); 4.59 (dd, J=13 and 2 Hz, 1H); 5.31 (d, J=1 Hz, 1H); 5.73 (d, J=1 Hz, 1H) ; 7.2–7.4 (m, 4H); 7.97 (s, 1H); 8.02 (s, 1H) ppm

Example 10

δ=0.4–0.6 (m, 2H) ; 0.75–0.95 (m, 2H) ; 4.5 (d, J–15 Hz, 1H); 4.52 (s, 1H); 5.02 (d, J=15 Hz, 1H); 5.32 (s, 1H); 5.71 (s, 1H) ; 6.44 (t, J=75 Hz, 1H) ; 7.1–7.4 (m, 4H) 8.05 (s, 1H); 8.3 (s, 1H) ppm

Example A

*Leptosphaeria nodorum* test (wheat)/protective

Solvent: 10 parts by weight of N-methyl-pyrrolidone

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the application rate indicated. After the spray coating has dried on, the plants are sprayed with a spore suspension of *Leptosphaeria nodorum*.

The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation.

Active compounds, active compound concentrations and test results are given in the table which follows.

TABLE A

| *Leptosphaeria nodorum* test (wheat)/protective | |
|---|---|
| Active compound | Degree of action (in %) of the untreated control at an application rate of 400 g of active compound/ha |
| according to the invention: | |

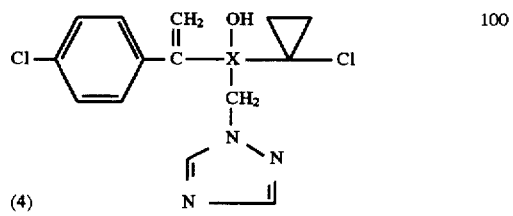

(4)                                          100

TABLE A-continued

| *Leptosphaeria nodorum* test (wheat)/protective | |
|---|---|
| Active compound | Degree of action (in %) of the untreated control at an application rate of 400 g of active compound/ha |

(6) [structure: 3-Cl-phenyl with CH2, OH, X, CH2, N-N-N triazole, Cl cyclopropyl]   100

(2) [structure: 2-F-phenyl with CH2, OH, X, CH2, triazole, Cl cyclopropyl]   100

(7) [structure: phenyl with CH2, OH, X, CH2, triazole, F cyclopropyl]   100

(8) [structure: 2-Cl-phenyl with CH2, OH, X, CH2, triazole, F cyclopropyl]   100

(9) [structure: 4-Cl-phenyl with CH2, OH, X, CH2, triazole, F cyclopropyl]   100

Example B

*Gibberella zeae* test (barley)/protective

Solvent: 10 parts by weight of N-methyl-pyrrolidone

Emulsifier: 0.6 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the application rate indicated. After the spray coating has dried on, the plants are sprayed with a conidia suspension of *Gibberella zeae*.

The plants are placed in a greenhouse under light-permeable incubation cages at a temperature of about 20° C. and a relative atmospheric humidity of about 100%.

Evaluation is effected 4 days after the inoculation.

Active compounds, application rates and test results are given in the table which follows.

TABLE B

*Gibberella zeae* test (barley)/protective (syn. *Fusarium graminearum*)

| Active compound | Degree of action (in %) of the untreated control at an application rate of 400 g of active compound/ha |
|---|---|
| according to the invention: | |
| 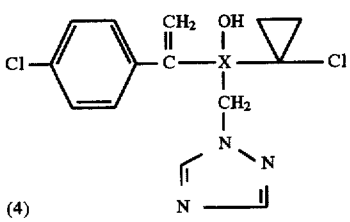  (4) | 100 |
| 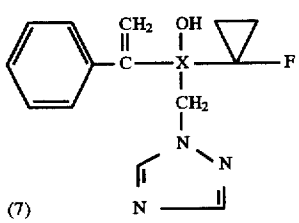  (7) | 100 |
| 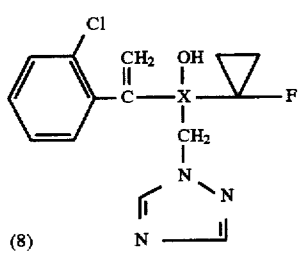  (8) | 100 |
|  (9) | 100 |

Example C

Podosphaera test (apple)/protective

Solvent: 4.7 parts by weight of acetone

Emulsifier: 0.3 parts by weight of alkyl-aryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated by dusting with conidia of the causative organism of apple mildew (*Podosphaera leucotricha*).

The plants are then placed in a greenhouse at 23° C. and a relative atmospheric humidity of about 70%.

Evaluation is carried out 10 days after the inoculation.

Active compounds, application rates and test results are given in the table which follows.

TABLE C

Podosphaera test/protective

| Active compound | Active compound concentration in the spray mixture in ppm | Degree of action (in %) of the untreated control |
|---|---|---|
| according to the invention | | |
| 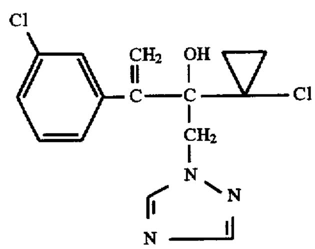  (6) | 1 | 100 |

Example D

Pyricularia test (rice)/protective

Solvent: 12.5 parts by weight of acetone

Emulsifier: 0.3 parts by weight of alkyl-aryl polyglycol ether

To produce a suitable preparation of active compound, 1 part by weight of active compound is mixed with the stated amounts of solvent and emulsifier, and the concentrate is diluted with water to the desired concentration.

To test for protective activity, young rice plants are sprayed with the preparation of active compound until dripping wet. After the spray coating has dried on, the plants are inoculated by spraying with an aqueous spore suspension of *Pyricularia oryzae*. The plants are then placed in a greenhouse at 100% relative atmospheric humidity and 25° C.

Evaluation of the disease infestation is carried out 4 days after the inoculation.

Active compounds, application rates and test results are given in the table which follows.

TABLE D

Pyricularia test (rice)/protective

| Active compound according to the invention | Active compound concentration in the spray mixture of % | Degree of action (in %) of the untreated control |
|---|---|---|
| (3) [structure: 2-Cl-phenyl-C(=CH₂)-C(OH)(CH₂-triazolyl)-cyclopropyl-Cl] | 0.025 | 70 |
| (4) [structure: 4-Cl-phenyl-C(=CH₂)-C(OH)(CH₂-triazolyl)-cyclopropyl-Cl] | 0.025 | 90 |

Example E

Pellicularia test (rice)/protective

Solvent: 12.5 parts by weight of acetone

Emulsifier: 0.3 parts by weight of alkylaryl polyglycol ether

To produce a suitable preparation of active compound, 1 part by weight of active compound is mixed with the stated amount of solvent, and the concentrate is diluted with water and the stated amount of emulsifier to the desired concentration.

To test for protective activity, young rice plants in the 3 to 4 leaf stage are sprayed until dripping wet. The plants remain in a greenhouse until the spray coating has dried on. The plants are then inoculated with *Pellicularia sasakii* and are placed at 25° C. and 100% relative atmospheric humidity.

The evaluation of the disease infestation is carried out 5 to 8 days after the inoculation.

Active compounds, application rates and test results are given in the table which follows.

TABLE E

Pellicularia test (rice)/protective

| Active compound according to the invention | Active compound concentration in the spray mixture of % | Degree of action (in %) of the untreated control |
|---|---|---|
| (3) [structure: 2-Cl-phenyl-C(=CH₂)-C(OH)(CH₂-triazolyl)-cyclopropyl-Cl] | 0.025 | 100 |
| (4) [structure: 4-Cl-phenyl-C(=CH₂)-C(OH)(CH₂-triazolyl)-cyclopropyl-Cl] | 0.025 | 90 |
| (6) [structure: 3-Cl-phenyl-C(=CH₂)-C(OH)(CH₂-triazolyl)-cyclopropyl-Cl] | 0.025 | 100 |
| (2) [structure: 2-F-phenyl-C(=CH₂)-C(OH)(CH₂-triazolyl)-cyclopropyl-Cl] | 0.025 | 100 |

We claim:

1. A hydroxyethyl-azolyl derivative of the formula

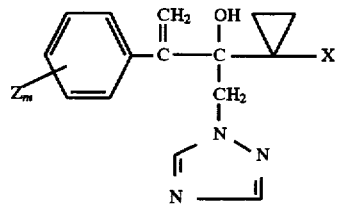

in which

X represents fluorine or chlorine,

Z represents fluorine, chlorine, bromine or difluoromethoxy, and m represents the numbers 0 or 1.

2. A fungicidal composition comprising a fungicidally effective amount of a compound according to claim 1 and an inert diluent.

3. A method of combating fungi in plant protection said method comprising applying to such fungi or to their habitat a fungicidally effective amount of a compound according to claim 1.

* * * * *